United States Patent [19]
Bensimon et al.

[11] Patent Number: 5,866,328
[45] Date of Patent: Feb. 2, 1999

[54] FAST DNA SEQUENCE DETERMINATION METHOD BY MEASURING ENERGY OF BASE PAIRING OR UNPAIRING OF NUCLEIC ACID SEQUENCES AND USE THEREOF IN SEQUENCING AND DIAGNOSTICS

[75] Inventors: Aaron Bensimon; David Bensimon, both of Paris; Vincent Croquette; Arnaud Chiffaudel, both of Antony, all of France

[73] Assignee: Centre National de la Recherche Scientifique, Paris, France

[21] Appl. No.: 532,751
[22] PCT Filed: Apr. 6, 1994
[86] PCT No.: PCT/FR94/00382
  § 371 Date: Feb. 12, 1996
  § 102(e) Date: Feb. 12, 1996
[87] PCT Pub. No.: WO94/23065
  PCT Pub. Date: Oct. 13, 1994

[30] Foreign Application Priority Data
  Apr. 6, 1993 [FR] France .................. 93 04056

[51] Int. Cl.⁶ .................. C12Q 1/68; G01N 33/48
[52] U.S. Cl. .................. 435/6; 436/94
[58] Field of Search .................. 435/6, 810; 436/94

[56] References Cited

U.S. PATENT DOCUMENTS

| | | | |
|---|---|---|---|
| 5,106,729 | 4/1992 | Lindsay et al. | 435/6 |
| 5,372,930 | 12/1994 | Colton et al. | 435/6 |
| 5,620,854 | 4/1997 | Holzrichter et al. | 435/6 |
| 5,624,711 | 4/1997 | Sundberg et al. | 427/261 |

FOREIGN PATENT DOCUMENTS

| | | |
|---|---|---|
| 0 397 416 | 11/1990 | European Pat. Off. . |
| WO94/16101 | 7/1994 | European Pat. Off. . |
| WO97/06278 | 2/1997 | WIPO . |

OTHER PUBLICATIONS

Steven B. Smith et al., "Direct Mechanical Measurements of the Elasticity of Single DNA Molecules by Using Magnetic Beads", Science, vol. 258, Nov. 1992, pp. 1122–1126.

Hansma et al., Science 256, 1180–1184 (1992).

*Primary Examiner*—Kenneth R. Horlick
*Attorney, Agent, or Firm*—Finnegan, Henderson, Farabow, Garrett & Dunner, L.L.P.

[57] ABSTRACT

A method for determining a DNA or RNA sequence, comprising determining the paring or separating energy between each base pair of the DNA or a double-stranded RNA/DNA hybrid corresponding to the DNA or RNA sequence to be determined, and comparing said energy with predetermined values.

80 Claims, 7 Drawing Sheets

FAST DNA SEQUENCE DETERMINATION METHOD BY MEASURING ENERGY OF BASE PAIRING OR UNPAIRING OF NUCLEIC ACID SEQUENCES AND USE THEREOF IN SEQUENCING AND DIAGNOSTICS

BACKGROUND OF THE INVENTION

The present invention relates to a fast method for the determination of a sequence of a nucleic acid, DNA or RNA, which is useful, in particular, for the sequencing of an unknown DNA or RNA or alternatively for the detection of a specific DNA or RNA sequence for diagnosis.

DNA sequencing is a major objective of molecular biology, and is at the heart of the human genome sequencing project.

Furthermore, demonstration of the presence of a specific DNA sequence in a physiological sample constitutes, at the present time, the major line of development of diagnostic methods. After the immunological technique, attention is now being turned to diagnostic methods that demonstrate modifications of the DNA itself in order to prevent, in particular, antibiotic resistance (see Nature, 1992, 358, p. 591), genetic abnormalities, the risks of cancer associated with genetic modifications and viral infections, for example infections associated with HIV or with hepatitis viruses.

These diagnostic methods comprise, at the present time, the so-called "direct hybridization" methods, which will detect the presence of this sequence by direct hybridization of a probe with the sample. The method is cumbersome and imprecise, in particular because it necessitates a detection by gel and exposure on light-sensitive film or radioactive counting.

Methods employing an amplification, in particular the PCR method, which, before the demonstration of the sequence by hybridization, will first amplify the corresponding portion of the DNA using, for example, primers and a polymerase, are excessively sensitive to contamination.

These methods have, in addition, the drawback of being indirect recognition systems, because the desired sequence is recognized only via the use of A probe.

SUMMARY OF THE INVENTION

The method according to the present invention makes it possible to demonstrate the hybridization or the nucleotide sequence should this be necessary. Hence, there cannot be any bias or ambiguity. This considerable progress is due to the fact that, for the first time, it is almost as fast to demonstrate the nucleotide structure of the desired sequence directly as to demonstrate it indirectly, for example using a probe.

It is even possible, as a result of the method of the invention, to demonstrate directly the hybridization between two complementary sequences without resorting to complete sequencing of this sequence.

Nucleic acid sequencing is nowadays carried out chiefly by the so-called Sanger method well known to biologists. In this technique, the DNA to be sequenced is first cut into small segments (of approximately 5 kb), which are then cloned into plasmids inserted into a bacterial strain. The plasmids are amplified in this strain and extracted. The inserted DNA is then copied from a plasmid promoter. This transcription is interrupted after the insertion of a random number of nucleotides. This consequently gives rise to a population of all the possible interrupted copies of the initial DNA. This population is separated by gel electrophoresis according to the molecular weight of the numerous copies. The position of the nucleotides along the DNA is read directly on the gel for each DNA fragment.

This process is very laborious. For a DNA of approximately 15,000 base pairs (15 kbp), the final step (after extraction of the plasmids) alone takes a week. Consequently, it is commonly accepted that the sequencing of a DNA comes to approximately 5 francs per base pair at the date of filing of the present application.

The method according to the present invention, based on physical techniques and electronic treatments, differs from the current approaches, which are chemical or biochemical. Its advantages are numerous:

1) It permits equally well the sequencing of short sequences and the sequencing of very long genes (greater than 10 kbp) without having to segment them into small pieces, as is the case in the present methods.
2) It is 10,000 times as fast. Present biochemical methods enable approximately 15,000 bases to be sequenced in a week. The method enables approximately 100 of them to be sequenced in a second, that is to say 60 million in a week.
3) It requires a very small amount of DNA.
4) It may be readily adapted and has a large number of degrees of freedom.
5) It can be readily automated, it being possible for the sequencing signal to be processed directly by computer.
6) It is potentially much less expensive than the present technique, since it does not require lengthy and laborious biochemical manipulations. Since the sequencing time is a decisive part of its cost, the method should be at least 1,000 times less expensive.

The present invention relates to a method for the determination of a DNA or RNA sequence, characterized in that the energy of pairing or of unpairing between each base pair of the double-stranded DNA or of a double-stranded RNA/DNA hybrid corresponding to the DNA or RNA sequence to be determined is determined, and in that this energy is compared with predetermined values.

This method affords several embodiments. In the first embodiment, each measured energy may be assigned a predetermined value, which corresponds to a base pair in the presence of corresponding neighboring bases; the nucleotide sequence of the DNA or RNA in question is thereby reconstructed.

In a second embodiment of the method, it is sought to demonstrate the presence of a known sequence. In this case, the essential features of this desired sequence may simply have been determined in order to make a "fingerprint" thereof, and it can then be enough to check whether or not the DNA or RNA sample to be determined has the same fingerprint.

In a third embodiment of the method, the global energy needed to unpair the double-stranded DNA or the double-stranded DNA/RNA hybrid is determined, and this global energy is compared with a threshold value of this energy corresponding to the same sequences fully paired, thereby enabling DNA/DNA or RNA/DNA complexes not fully paired, whose energy of unpairing is less than the threshold value, to be ruled out; the "fingerprint" in question will be referred to as the "global fingerprint", or signal.

The latter two embodiments of the method are intended more especially for diagnosis, that is to say for demonstration of the presence or absence of a known sequence, whereas the first embodiment is intended more especially for sequencing.

DETAILED DESCRIPTION

"Energy of pairing or of unpairing" is understood to denote essentially the energy needed to separate or recover by re-forming ("re-pairing") two base pairs, which are paired on two complementary strands of DNA or of a DNA/RNA hybrid.

The invention is based on the demonstration that it is possible to measure, quickly and reliably, the bonding force of each base pair of a double-stranded DNA or of a DNA/RNA hybrid and to assign a specific sequence to each of these values, the bonding force depending not only on the base pair in question but also on its environment, in particular on the neighboring bases and, where appropriate, on the experimental conditions under which the pairing or unpairing takes place.

In effect, DNA is a double helix formed by two strands composed of the nucleic acids adenine, thymine, guanine and cytosine, the cohesion of which is produced, on the one hand by the hydrogen bonds between the base pairs adenine (A)/thymine (T)—two bonds—and the pairs guanine (G)/cytosine (C)—three bonds—; and on the other hand by bonds due to the stacking energies of the different base pairs. Table 1 gives an idea of the corresponding energies for DNA. It is seen that these energies vary significantly according to the base pairs and the neighboring bases. The results in this Table correspond to the measured energies for unpairing dimers formed from two adjacent bases. Reference may also be made to the work by W. Saenger (Principles of Nucleic Acid Structure 1988, published by Springer-Verlag). The arrows in the Table represent the direction of reading of the DNA.

TABLE 1

| Dimers | | Energies (kJ × mole⁻¹ × dimer⁻¹) |
|---|---|---|
| ↑C.G↑ ↓G.C↓ | | −60.99 |
| ↑C.G↑ ↓A.T↓ | ↑T.A↑ ↓G.C↓ | −43.93 |
| ↑C.G↑ ↓T.A↓ | ↑A.T↑ ↓G.C↓ | −41.01 |
| ↑G.C↑ ↓C.G↓ | | −40.50 |
| ↑G.C↑ ↓G.C↓ | ↑C.G↑ ↓C.G↓ | −34.53 |
| ↑T.A↑ ↓A.T↓ | | −27.46 |
| ↑G.C↑ ↓T.A↓ | ↑A.T↑ ↓C.G↓ | −27.46 |
| ↑G.C↑ ↓T.A↓ | ↑T.A↑ ↓C.G↓ | −28.34 |
| ↑A.T↑ ↓A.T↓ | ↑T.A↑ ↓T.A↓ | −22.45 |
| ↑A.T↑ ↓T.A↓ | | −15.97 |

This method possesses two essential variants.

In the first embodiment, the energy of unpairing between each base pair of the DNA or DNA/RNA hybrid is determined by attaching at least one base of each strand of the DNA or of the DNA/RNA hybrid to a support and moving away the supports so as to pull apart, one after another, each base pair while measuring at each unpairing the energy needed for unpairing and comparing it with predetermined values.

In the second embodiment, the energy of pairing between each base pair of the DNA or DNA/RNA hybrid is determined by attaching at least one base of each strand of the DNA or of the DNA/RNA hybrid to a support and bringing the supports together so as to pair each base pair while measuring at each pairing the energy needed for pairing and comparing it with predetermined values.

The attachment of each DNA strand to a support by at least one base may be carried out by direct attachment of said base to the support, but also by indirect attachment via an arm, which can be, for example, a peptide or an inert carbon chain, thereby avoiding effects associated with the surface of the support.

It is also possible to attach a segment of DNA or of RNA to a support by several bases.

Lastly, it will be preferable to attach each strand of the DNA by adjacent bases, but in some cases, especially when only a signal corresponding to a "global fingerprint" is sought, each DNA strand may be attached by bases located at opposite ends.

Naturally, it should be understood that, when the terms "energy of pairing or of unpairing" are used, this energy is to be determined, either directly, or indirectly by means of a variable. The latter can be, in particular, a force (in particular gravitational or magnetic) or a time or a temperature of pairing or of unpairing. Some of these variables may be associated with the movement of a spring or of a membrane or, in some cases, with variations of electrical or magnetic parameters.

If it is desired that the double-stranded DNA be represented diagrammatically in the context of the present invention, it is possible to liken it to a "zip fastener", which is opened (or closed) while measuring for each component the energy used on unpairing (or pairing).

The method according to the invention may be used for different applications.

In the first place, it may be used for the direct sequencing of an unknown nucleic acid. In this case, the predetermined values of the energies of pairing and of unpairing are measured beforehand for each base pair according to their environment, and one of the possible bases can then be directly assigned to each unpairing or pairing according to the energy measured.

In this type of sequencing, it can be advantageous, after pulling the two strands apart, to re-pair them again and then to measure the values of the bonding energies again so as to accumulate the data and thereby decrease the background.

It is also possible, in order to facilitate re-pairing, to arrange for the free ends of the double-stranded DNA to be joined to one another covalently or quasi-covalently before pulling apart, which makes it possible, in particular, to perform cycles of pairing and of unpairing and thus to improve the signal/noise ratio.

Techniques enabling the free ends of double-stranded DNA to be joined together are known, and some will be described in greater detail in what follows.

The method according to the present invention may also be used for diagnostic purposes to permit, in particular, the sequencing of variable regions of DNA corresponding to abnormalities being looked for; the technique is then similar to the one described above for sequencing.

However, it is possible to provide for a simplified technique, in which the values of the forces are recorded in the form of a "fingerprint" or signal, which will be compared with the fingerprint or signal being looked for, without the order and nature of the bases being expressly determined. If the fingerprint being looked for corresponds to the presence of an abnormality, any other fingerprint will be considered negative, or on the contrary a fingerprint corresponding to normal DNA may be adopted, considering any other fingerprint positive.

For diagnostic purposes, a simpler variant of the method described above may be used. This entails not measuring sequentially the energy needed for unpairing of the base pairs, but the total energy needed for unpairing two hybridized segments while pulling on their ends. To this end, a probe complementary to the target sequence sought in a DNA/RNA sample is grafted onto a support (by known methods). The single-stranded DNA/RNA of the sample is then hybridized with the probe, and one of its ends is thereafter anchored to an appropriate second surface (for example a magnetic bead coated with streptavidin, permitting quasi-covalent bonding with a previously biotinylated DNA). The total energy needed to "tear apart" the two hybridized segments serves as a "fingerprint" permitting identification of the hybridization.

Implementation of the method has been made possible, in particular, by the existence of the atomic force microscope (AFM), which enables the forces to be measured directly as will become apparent from the description.

The atomic force microscope (AFM) is an apparatus marketed by different companies (Park, Digital, and the like). It is used in general for visualizing a surface by scanning it with a very fine tip placed at the end of a lever.

Thus, one of the simplest means for pulling DNA and for measuring the force exerted consists in using an atomic force microscope (AFM), attaching one of the ends of the DNA molecule to the tip or the lever of the AFM and linking the other to the specimen-carrier surface rigidly fixed to the movable piezoelectric tube of the AFM. These methods enabling DNA to be attached to surfaces are known, and some of the methods that can be used are recalled below.

Bustamente et al., have described in Science (1992, vol. 258, p. 1122) a method of measuring the elasticity of double-stranded DNA employing a different means of stretching the DNA, based on viscous and magnetic forces.

The very principle of this method cannot be applied to sequencing, since there is no separation of the two DNA strands and the spatial resolution is insufficient (of the order of one micron).

By modifying the electrical voltage applied to the tube of the AFM, the tube moves and can thus pull with it one of the ends of the DNA if the latter has previously been attached on one side to the lever and on the other to the support. The traction thus imposed on the paired bases is transmitted to the lever of the AFM, the deflection of which permits an accurate measurement of this force. Since the typical elastic constant of the lever of an AFM is approximately $3 \times 10^{-2}$ N/m, and since the accuracy in the measurement of deflection of the lever can reach, for example, 0.2 Å, the accuracy in the measured force is better than $0.6 \times 10^{-12}$N, which is approximately 100 times lower than the interstrand pairing forces (produced by hydrogen bonds). Reference may be made to the article by J. N. Israelachvili (Inter-molecular and Surface Forces, published by Academic Press, 1985). The AFM is a useful tool for measuring this type of force, but it is not essential and may be replaced by any other sensitive method of force measurement, such as methods of capacitive detection or by magnetic levitation. Measurements of forces by the latter method are described by B. Gauthier-Manuel, Europhys. Conf. 14C C34, 1990.

The description below is given with reference to the AFM, but may be adapted to any other device.

The periodicity of the base pairs along the DNA molecule is 3.4 Å, and enables the influence of spurious effects to be limited. On pulling the two adjacent ends of the DNA strands, the force measured will have a periodic component (of period approximately 6.8 Å), modulated by the interstrand cohesion forces which reflect the sequence of the nucleic acids in the DNA. This periodic component may hence be used for the sequencing of DNA after calibration of these modulations with known DNA or RNA sequences, but also enables spurious effects to be eliminated.

In effect, the traction force on the lever depends on various spurious effects (for example van der Waals forces between the lever and the surface, and the like), in addition to the traction force due to the unwinding of the DNA. However, only the traction force of the DNA molecule on the lever is periodic with a period of approximately 6.8 Å. Signal filtering techniques make is it possible to eliminate the spurious effects having different frequencies. By calibrating once and for all the force signal measured for known DNA sequences, a correspondence is established between the amplitude of the periodic force and the DNA sequence. Measurement of the amplitude of the periodic signal can then be used to sequence unknown DNA fragments. At the end of the traction cycle, since the molecule remains anchored to the surfaces, it is also possible to measure a periodic force signal originating from the re-pairing of the base pairs when the two strands are brought together ("closing the zip fastener"). Thus, by repeating the cycles of stretching/bringing together (traction/relaxation), it is possible to improve signal/noise ratio and reliability of the sequencing.

Lastly, as has been pointed out above, it is possible, in order to vary the energies brought into play, to vary the conditions of implementation of the method, especially the conditions of the medium in which pairing and unpairing take place. Thus, by modifying the pH, the temperature, the ionic strength or the nature of the products added, it is possible to modify the values of the energies brought into play for the same base pair. In this case, it may, of course, be necessary to perform the reference measurements under the same conditions for calibration. However, the calibration values may, in some cases, be obtained by calculation or using nomograms or tables.

In order to attach DNA to surfaces or supports, use may be made of any one of the techniques known in the field. Essentially, two techniques may be distinguished:

1) The direct method

In this method, the DNA becomes anchored directly to the support, for example the tip of the AFM, which involves a functionalization of this surface, for example by coating it with streptavidin, a COOH group, and the like, capable of reacting with the functionalized end of the DNA.

2) The indirect method

The DNA is anchored to a particle, for example appropriate powder or microbead (where appropriate magnetic), which is itself then linked to the support, for example to the lever of the AFM. One of the methods enabling this linkage to be made consists in magnetizing the lever. This may be done by different direct techniques or by sticking a small magnet to its end. The indirect method makes possible, in particular, reversible coupling. By pulling sufficiently hard, the microbead detaches from the lever and the latter is free to couple a new microbead.

This method enables a heterogeneous population of DNA molecules (already anchored to the movable support) to be sequenced or tested in series, by coupling them (reversibly) one after another to the measuring surface (the lever of the AFM).

The direct methods necessitate, in general, functionalizing the DNA or RNA, especially the 3' and 5' ends, that is to say grafting appropriate chemical groups onto them. It is, moreover, preferable to join the other two free ends of the molecule by a loop in order to prevent the strands from dissociating at the end of the operation, so that the latter can be repeated if appropriate. For this purpose, different procedures may be adopted.

The simplest is to functionalize, using synthetic oligonucleotides, one of the ends of a double-stranded DNA with two different functions (biotin and amine, for example), which permit anchoring to two different pre-treated surfaces. The two strands at the other end may be joined using a partially paired synthetic nucleotide in the form of a loop. In this way, a paired, single-stranded DNA is produced from a double-stranded DNA (see FIG. 2($a$)). The advantage of this method lies in its capacity to functionalize a heterogeneous population of large DNA fragments (as are obtained by fractionation of a gene or chromosome), which can then be analyzed simultaneously. In this case, the DNA sample is fractionated using two (or more) restriction enzymes, which enables a subpopulation to be obtained with two different restriction sites at its ends which are similar over all the fragments. This enables the two ends to be treated differently (for example by joining one of end to an oligonucleotide in the form of a loop possessing the appropriate restriction site at its end). The drawback of this method lies in the steric interference between the two adjacent functional groups, which can make coupling to the surfaces difficult.

This problem may be solved by the following method:

A double-stranded DNA (symbolized here: a/a') is converted to a dimer aa'/a'a through the addition of complementary oligonucleotides at the end of the chain, as is shown diagrammatically in FIG. 2($b$). To this end, two DNA populations a/a' are considered. In one, the 5' end of strand a is functionalized with a reactive group A, and its 3' end with an oligonucleotide b. In the other, the 3' end of strand a' is functionalized with a reactive group B different from A, and its 5' end with an oligonucleotide complementary to b:b'. Hybridization and ligation of these two populations produces a DNA aba'/a'b'a, one of the strands (aba') of which is functionalized at both of its ends with two different reactive groups A and B enabling it to be anchored to two different surfaces.

To obtain the same configuration as in the previous method, the two strands (aa' and a'a) must be dissociated, for example by denaturing the DNA. Since the two halves of the dimer of single-stranded DNA (aa') (which is coupled to both surfaces) are complementary (by construction), they pair spontaneously as in the initial DNA (a/a') (see FIG. 1($a$)). By moving one of the surfaces, the DNA is unwound ("the zip fastener is opened") and the force exerted on the other surface, kept stationary, is measured.

As regards the actual anchoring techniques, there are many of these and they derive from the techniques for anchoring macromolecules (proteins, DNA, and the like) to commercially available pretreated surfaces. Most of these techniques have been developed for immunology tests, and link proteins (immunoglobulins) to surfaces carrying groups (—COOH, —NH$_2$, —OH, and the like) capable of reacting with the carboxyl (—COOH) or amine (—NH$_2$) ends of proteins.

The covalent anchoring of DNA may be accomplished directly, via the free phosphate of the 5' end of the molecule, which reacts with a secondary amine (Covalink —NH surface marketed by Polylabo at Strasbourg) to form a covalent bond. It is also possible to functionalize DNA with an amine group and then to proceed as with a protein.

There are also surfaces coated with streptavidin (Dynal beads, and the like), which permit quasi-covalent anchoring between the streptavidin and a biotinylated DNA molecule. Lastly, by grafting an antibody directed against digoxigenin onto a surface (by the methods mentioned above), a DNA functionalized with digoxigenin may be anchored thereto. This represents merely a sample of the many possible anchoring techniques.

Among the attachment and anchoring techniques, there should also be mentioned, for example, the techniques described in Patent EP 152,886 using an enzymatic coupling for the attachment of DNA to a solid support such as cellulose.

Patent EP 146,815 also describes various methods of attachment of DNA to a support.

Similarly, Patent WO 92/16659 proposes a method using a polymer to attach DNA.

Naturally, the DNA may be attached directly to the support but, where necessary, especially with a view to limiting the influence of the surfaces, the DNA may be attached at the end of an inert arm of peptide or other nature, as is, for example, described in Patent EP 329,198.

The present invention also relates to a diagnostic kit containing one or more of the following components:

a known nucleotide sequence (or "primer") capable of hybridizing under stringent conditions with a test single-stranded DNA or RNA containing all or part of said sequence in a reaction medium containing other nucleic acids or after separation of said nonhybridizable nucleic acids, a DNA or RNA in double-stranded form as reference standard component, consisting of the hybridizable sequence looked for in the sample, a support enabling the DNA or RNA of the test sample or the primer ("known nucleotide sequence") to be attached, at least one restriction enzyme, oligonucleotides to functionalize the ends of the test DNA or RNA, or an already functionalized primer, a surface that can be attached to the functionalized end of the DNA or RNA or the primer to be hybridized.

It also relates to an intermediate, which is useful for calibrating the method. This is a double-stranded DNA whose normally adjacent 5' and 3' ends are, in the one case joined covalently or quasi-covalently by an oligonucleotide in the form of a loop, and in the other case joined to one or more separate solid supports.

The examples below will enable other features and advantages of the present invention to be brought out.

EXAMPLE 1

Figure 3:
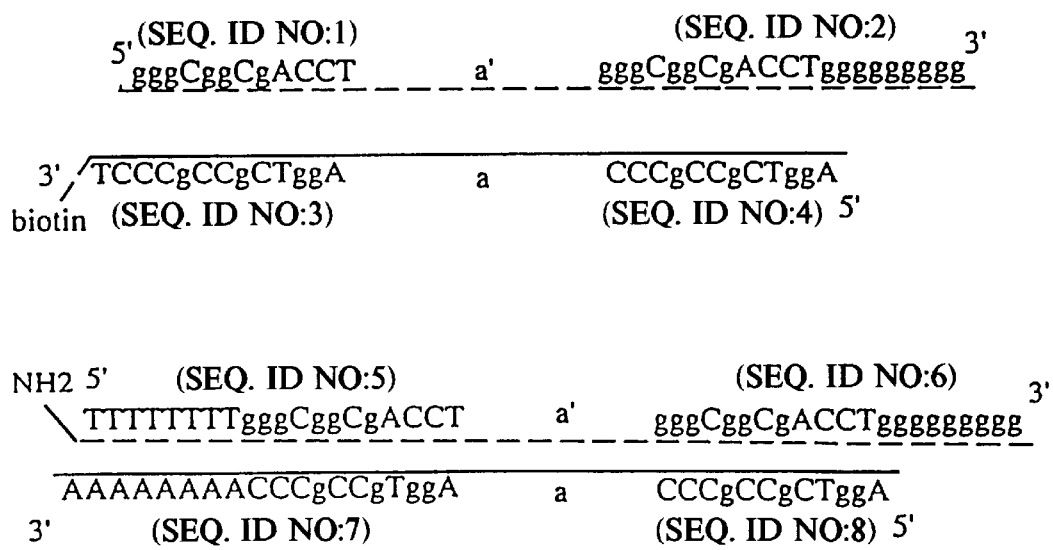
FIG. 3 shows diagrammatically the construction of the DNA diner described in 2(b) applied to phage lambda DNA.

In this example, the DNA chosen is phage $\lambda$ DNA ($\lambda$ DNA), which comprises 48,502 base pairs, the sequence of which is known. The two strands a and a' of this DNA in its linear (open) configuration have 12 unpaired bases at their 5' end. The ends of this DNA may be readily functionalized, as is shown diagrammatically in FIG. 3. Using synthetic oligonucleotides complementary to the unpaired ends of this DNA, the 5' end of strand a and the 3' end of the complementary strand a' are in the one case biotinylated and in the other case aminated. Synthetic oligonucleotides b and b' (partially complementary to the free end of these DNAs) are then paired and linked. Finally, the two DNAs are hybridized and linked. The oligonucleotides are shown in bold lines and their sequence in italics.

When this has been done, the functionalized DNA is anchored (through biotin, amine or digoxigenin groups) to the surface of pretreated polystyrene beads (marketed, inter alia, by Dynal and Rhône-Poulenc under the brand name (Estapor). The latter are coated either with streptavidin, which has a quasi-covalent affinity for biotin, or with a monoclonal antibody permitting binding with another antibody directed against digoxigenin (DIG), or alternatively with carboxyl groups (COOH), which form a covalent bond with an amine group ($NH_2$), as is described below under Materials and Methods.

Figure 1:
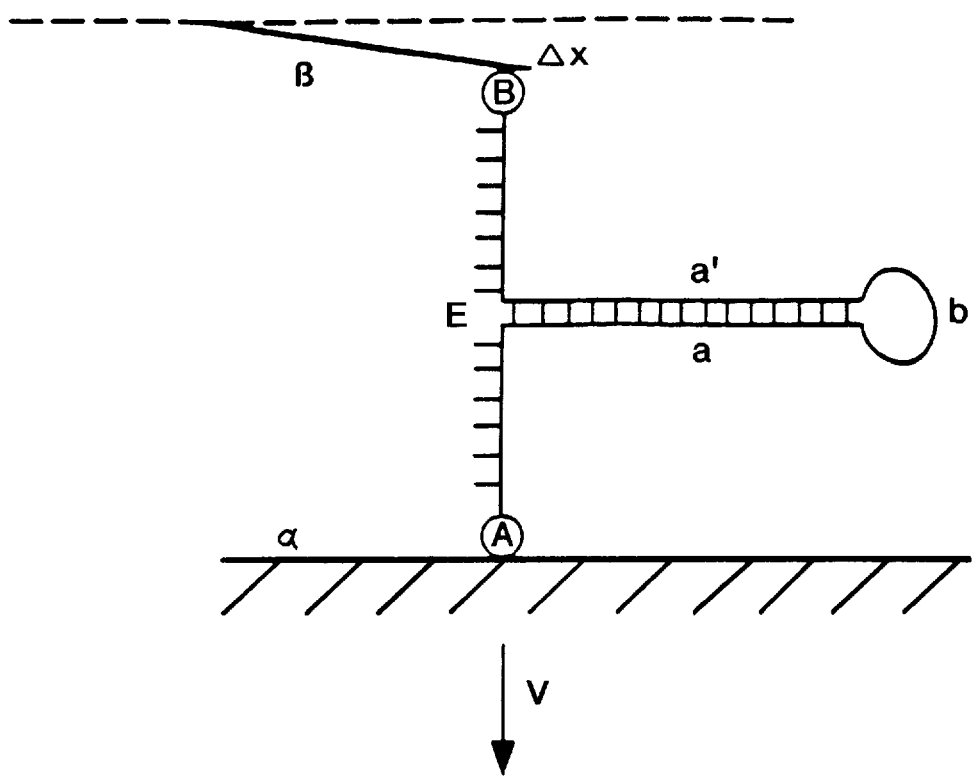
FIG. 1 is a diagram of the method employing an atomic force microscope.
Figure 2A:
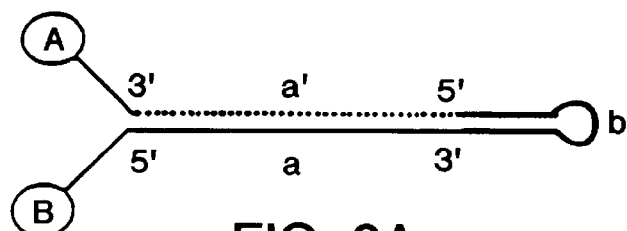
FIGS. 2A and 2B show diagrammatically two methods of functionalization of DNA with terminal groups.
Figure 2B:
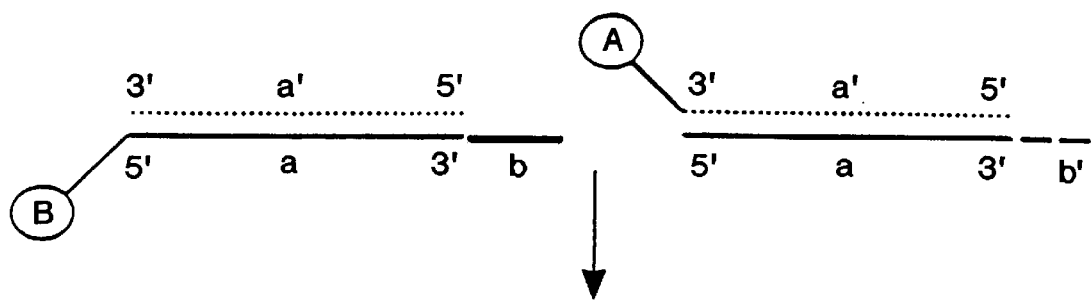
Figure 2B:
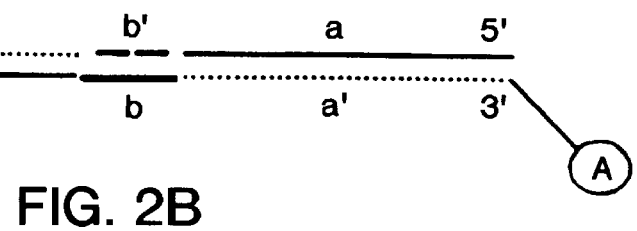

In order to pull a single strand of a DNA dimer (aa'), as shown diagrammatically in FIG. 1, one of its ends is anchored to a pretreated flat surface $\alpha$ via a link by means of functionalization with an amine group A, and the other end is anchored to a streptavidin-coated Dynal magnetic bead B. A small magnet stuck to the end of the lever of an AFM enables linkage between the lever and the Dynal bead to be maintained. Since the two strands a and a' are complementary, they are partially paired. The surface $\alpha$ is driven at a velocity v, and the traction force on the DNA measured by the deflections of the surface $\beta$, which acts as a spring (for example the lever of an AFM). The bases of the DNA unpair at the point E. Measurement of the movement and of the force is accomplished by means of the AFM.

EXAMPLE 2

Materials and Methods $\lambda$ DNA is obtained from Boehringer-Mannheim. The oligonucleotides complementary to the cos end of phage lambda DNA were synthesized (oligo1: 5'-AGGTCGCCGCCC-3'(SEQ ID NO:9) 12-mer; oligo2: 5'-GGGCGGCGACCT-3'(SEQ ID NO:10) 12-mer). All the enzymes employed are obtained from Boehringer-Mannheim and Bio-Labs. $^{32}$P Nucleotides are obtained from Amersham. All the magnetic beads are obtained from Dynal (Dynabeads M-280 Streptavidin: Dynabeads M-450 sheep anti-Mouse IgG). Latex particles are obtained from Rhône-Poulenc (Estapor). Anti-DIG immunoglobulin (monoclonal antibody is obtained from Boehringer-Mannheim. Covalink NH modules are obtained from Nunc, and plates of different batches were employed. All reagents are obtained from Sigma. Labeled material was purified on a P-6 spin column (Bio-Rad).

Functionalization of the Ends of the DNA

In order to functionalize the two ends of a $\lambda$ DNA molecule in a different way, the following method was employed:

1) Labeling of the end of the molecule with a Klenow fragment 0.08 nmol (2.5 $\mu$g) of $\lambda$ DNA are labeled at their end with 2 units of Klenow fragment in the presence of 2 nmol of biotin-dUTP (or Dig-dUTP or amino-dUTP) and the radioactive nucleotides, dCTP or dGTP (3000 Ci/mmol), so as to evaluate the yield of the different reactions. This reactions are conducted under standard conditions for labeling of the ends. the labeled DNAs are purified from the free nucleotides on a spin column. The labeled DNAs are fragmented into two fragments (45 kbp and 3 kbp) with 4 units of restriction enzyme KAS1 at 37° C. for 4 to 6 hours. The two fragments are separated on 1.5% low-melting agarose, eluted and concentrated with an Elutip column. The fragments thereby obtained possess two different ends (one with a 5'-phosphate and another with a biotin, DIG or an amino group close to the 3' end). They may be linked to active surfaces as described below or employed to perform dimer constructions by ligation of two fragments: one with the biotin (for example) end, and the other with a DIG group on the other end.

2) Labeling of the ends with modified oligonucleotides 10 nmol of oligonucleotides homologous to the two cos ends of λ DNA are modified at their end. All the oligonucleotides are phosphorylated at the 5' end by a kinase reaction. 1 nmol of oligonucleotides is incubated at 37° C. for 3 to 4 hours in the presence of 200 nmol of ATP (radioactively labeled with 16 pmol of γ-ATP$^{32}$ –3000 Ci/mmol) and 10 μl of T$_4$ polynucleotide kinase. These oligonucleotides phosphorylated at the 5' end are purified from the free nucleotides on a spin column. Their 3' end is then modified by incorporation of biotin-dUTP, DIG-dUTP or amino-dUTP. 10 pmol of oligonucleotides phosphorylated at the 5' end are incubated at 37° C. for 1 to 2 hours in the presence of 10 nmol of biotin-dUTP (DIG-UTP or amino-dUTP) and 2 units of deoxytransferase terminal enzyme. The modified oligonucleotides are purified from the free nucleotides on a spin column.

2 pmol of these modified oligonucleotides are linked with 0.1 pmol of λ DNA in the presence of 5 units of T$_4$ ligase at 16° C. for 12 hours in a reaction volume of 200 μl. Unlinked oligonucleotides are separated from the labeled DNA by two successive precipitations in an ammonium acetate/isopropanol mixture. The DNA is cleaned in cold 70% ethanol, dried in a "speed-vac" and suspended in distilled water.

Anchoring of the Surface

The functionalized DNAs described above may have 4 different functional groups (5' phosphate, biotin, DIG and NH$_2$) which are capable of reacting with commercially available pretreated surfaces.

1) Anchoring of the biotin group to streptavidin-coated surfaces

Streptavidin-coated Dynal M-280 beads are washed three times in 1×PBS solution (pH 7.4)+0.1% BSA. The beads are collected with a Dynal magnetic particle concentrator, resuspended in TE solution+2 mol of NaCl and incubated in a rotator with the modified DNA (at different DNA molecules/beads ratios) at room temperature for 1 to 2 hours.

2) Anchoring of DIG to anti-DIG-coated surfaces

Dynal M-450 beads coated with a sheep anti-mouse IgG are cleaned according to the information supplied by Dynal. 100 ml of a solution of beads (approximately 4×10$^7$ beads) are incubated in a rotator at 4° C. for 12 hours with 10 μg of anti-DIG IgG (approximately 10$^{-10}$ mol). The beads are then cleaned in PBS/BSA solution and resuspended in PBS. DIG-labeled DNA is then incubated with the beads (at different ratios) in a rotator at room temperature for 4 hours.

3) Anchoring of amino groups to COOH acid surfaces

COOH Estapor latex particles (diameter 1.1 and 2 μm) are cleaned twice by centrifugation in distilled water and pre-activated with 3-(dimethylaminopropyl)carbodiimide (CDI). This step is performed by incubating 0.1 ml of cleaned beads with 0.1 mg of CDI at 50° C. for 1 hour. The preactivated particles are cleaned three times by centrifuging a 0.05 mol solution of morpholinoethanesulfonic (MES) at pH 5.5. The precipitated beads are resuspended in 100 μl of TPG (0.05 mol NaH$_2$PO$_4$.2H$_2$O; 0.1% NaCl; 2% gelatin; pH 6.6).

The beads can then form covalent bonds with the amino groups present in the protein and the amino groups of the modified DNAs. 100 μl of a latex solution (approximately 10$^9$ beads) are incubated in the presence of 0.5 mg of avidin (or 0.5 mg of protein A or 0.25 pmol of amino-modified oligo2) at 50° C. for 1 hour, and then kept rotating at room temperature for 12 hours. The linked beads are then cleaned 3 times with TPG buffer, resuspended in 100 μl of TPG and maintained at 4° C. The avidin-coated beads are linked to the DNAs modified with biotin, as described above. The protein A-coated beads are coated with an anti-DIG IgG by incubation with 0.1 mg/ml of antibody at room temperature for 12 hours. Lastly, linking with DIG-modified DNA is performed as described above.

4) Anchoring of 5' phosphate groups to surfaces activated with a secondary amine (NH) (Nunc Covalink modules)

Different amounts of λ DNA (from 50 ng to 0.005 ng) are dissolved in 75 μl of 10 mmol solution of 1-methylimidazole (1-MeIM) and 25 μl of 0.2M 1-ethyl-3-(dimethylaminopropyl)carbodiimide (EDC). This solution is introduced into a Nunc Covalink well. The modules are incubated at 50° C. for 5 to 6 hours, followed by 3 cleanings with 5×SSC, 0.25% SDS solution (pre-heated to 50° C.) and 3 cleanings with 0.1×TE.

In order to avoid nonspecific binding of the preactivated beads at the surface of the well, 0.1% BSA solution is added and incubated at room temperature for 12 hours. The wells are cleaned 3 to 5 times with 0.1×TE. Biotin-labeled DNAs are denatured in 0.25 mol NaOH solution so as to free the biotin 3' ends. Streptavidin-coated M-280 beads are then added to link with the biotin end and are incubated at room temperature for 0.5 hour. Unlinked beads are harvested by a magnetic means. The DNA linked by its 5' phosphate end to the surface of the well and by its biotin-labeled 3' end to the surface of the beads is now ready for manipulation.

Magnetization of the Lever

In order to withdraw selectively the attached M-280 paramagnetic beads, the AFM lever is magnetized as follows: using a micropipette at the end of a micromanipulator (Leitz) and under a microscope (Reichert-Jung Polyvar), a small drop of an ultraviolet-curing adhesive (Norland Optical Adhesive) is deposited on the tip of the AFM (Park) cantilever. A small magnetic particle (radius approximately 7 μm) (a cobalt bead or a grain of powdered SmCo magnet) is taken with the micropipette, placed on the drop of adhesive, and polymerized by UV illumination for approximately 20 minutes. The magnetized lever is employed to withdraw the particles linked to the Covalink surface, and placed in a magnetic field under an inverted optical microscope (Nikon) or an AFM (Park Scientific Instruments, USA).

EXAMPLE 3

Results

An atomic force microscope (AFM) consisting essentially of a small elastic lever (cantilever) 100 to 200 μm long and 0.6 μm thick is used. The position of the fixed end of the lever is controlled at around 10$^{-11}$ m relative to the sample by means of a piezoelectric tube. The deflection of the movable end, measured optically, enables the force applied to be detected with sensitivity in the vicinity of 10$^{-12}$N. At the latter end, the traditional probe of the AFM (a silicon nitride tip with a radius of curvature of a few tens of nanometers) has been replaced by a ferromagnetic cobalt bead 7 μm in diameter. This assembly constitutes a magnetic force sensor. This magnetic sensor can be attracted by a 2.8 μm Dynal bead attached to a solid substrate giving rise to a deflection of the spring. Conversely, the sensor can attract a Dynal bead in solution or partially free at the end of a DNA strand. There is then little or no deflection, and the bead becomes stuck spontaneously to the sensor. The first type of interaction is measurable directly by the AFM, the second can be observed visually in an optical microscope.

Figure 4:
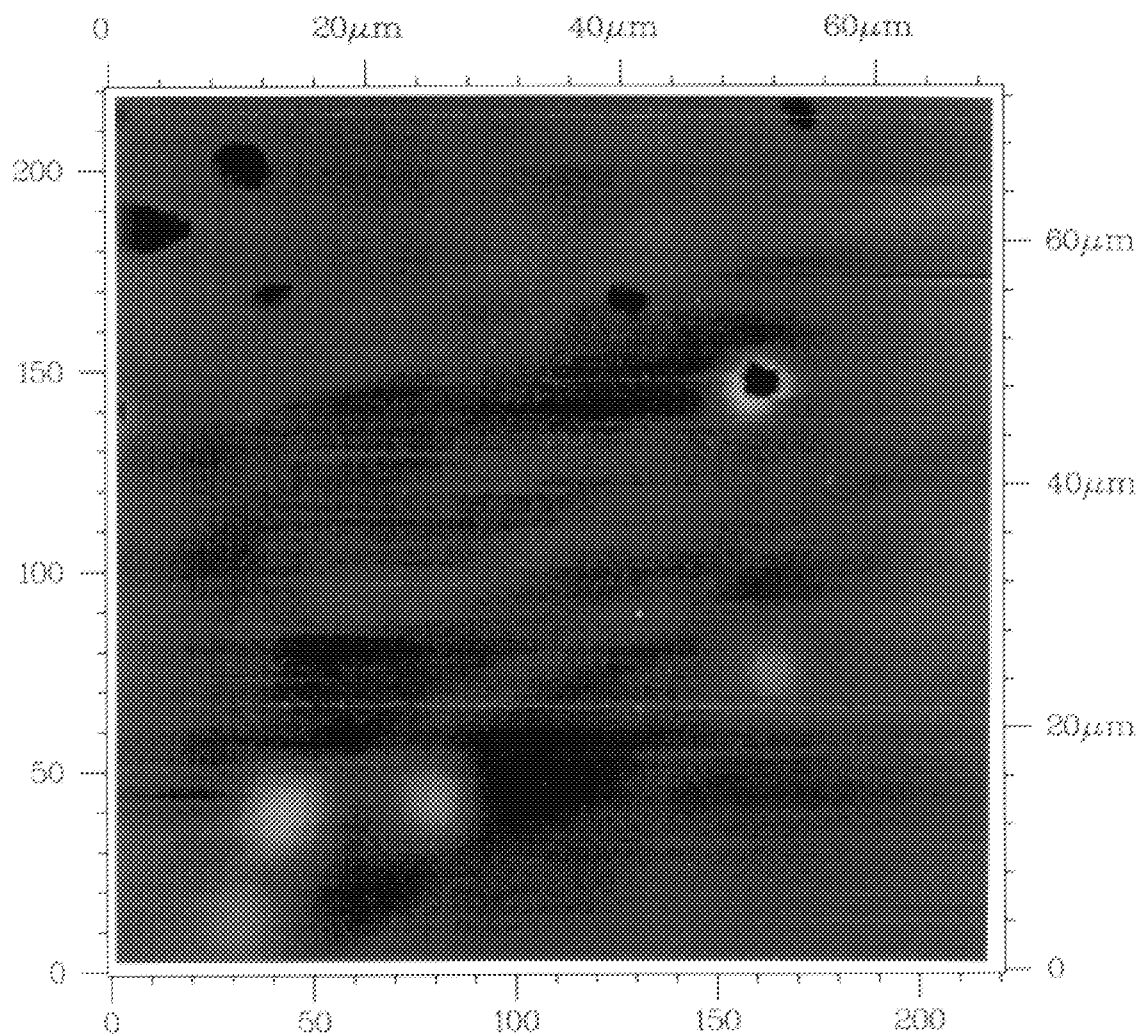
FIG. 4 shows a magnetic image formed between approximately 3 $\mu$m above the substrate. The white beads at the bottom of the image are observed without direct contact (magnetic attraction), while the black ones at the top are observed by direct contact (repulsive force of contact). The imaged beads are 2.8 $\mu$m in diameter.
Figure 5A:
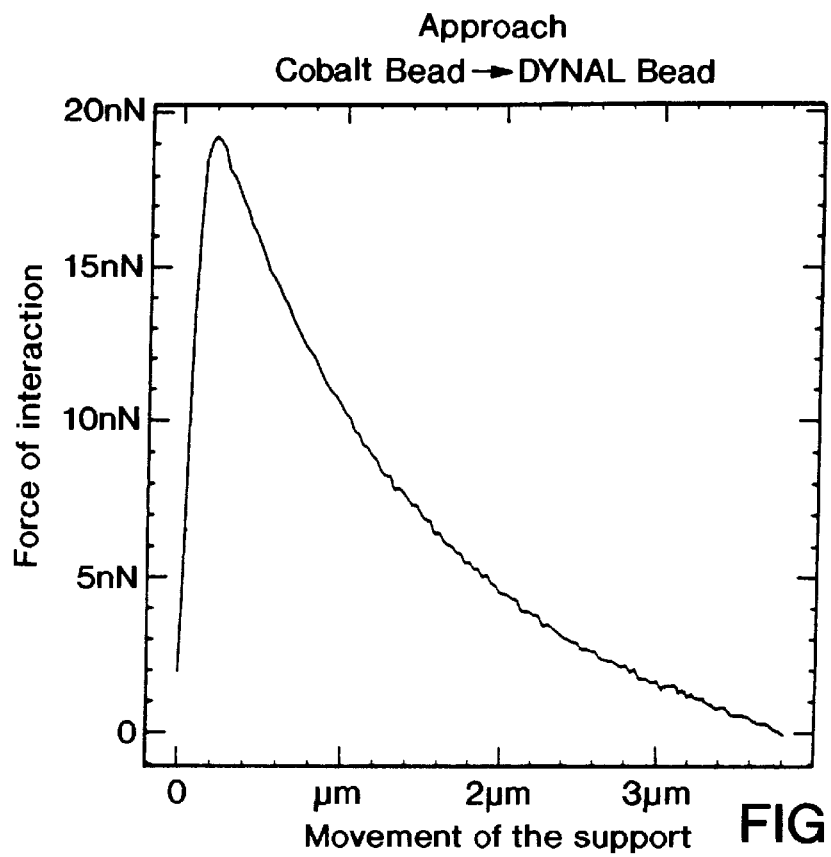
FIGS. 5A AND 5B show approaches made with the force sensor vertically with respect to the center of a bead (a) or of the unreacted substrate (b). A magnetic field is applied. In each graph, the continuous curve represents the approach from a position a few microns away from the substrate; the dotted curve represents the return. In (a), the magnetic attraction manifests itself in a rise in the curve above the value a long distance away. In (a) and (b), the repulsion (on contact) manifests itself in a rapid fall in the value of the force.
Figure 5B:
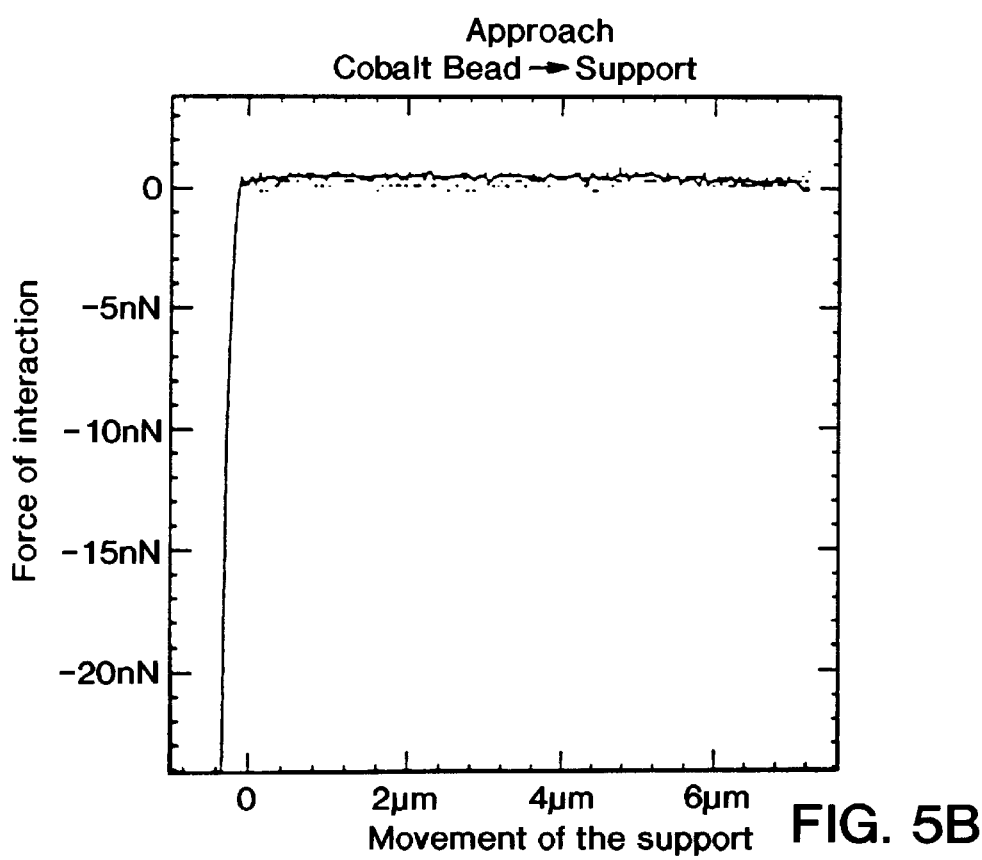

The Dynal beads may be rendered rigidly fixed to the activated substrate (Nunc Covalink modules) by direct biochemical bonding or by nonspecific adhesion. This adhesion is strengthened by the field gradients of a small magnet located a few millimeters under the substrate. The force of attraction between the sensor and a bead, which is maximal at the limit of contact, reaches $10^{-8}$ to $10^{-9}$N. In the absence of a magnetic field, the range of the (permanent dipole-induced dipole) interaction is very small relative to the diameters of the beads and is hence difficult to measure. In contrast, a small field saturates the magnetization of the induced dipoles, thereby increasing the range, which reaches approximately $4\mu$. It is then possible to produce images by scanning with the sensor a plane located 1 or $2\mu$ above the bead (see FIG. 4). This permits a very fine localization of the beads, which can then be approached. FIG. 5 shows approaches made vertically with respect to the center of a bead and/or the unreacted support. In (a), there is seen, from right to left, the magnetic attraction at a distance followed by the contact of the sensor with the bead. In (b), only the contact of the sensor with the support is detected. In the absence of a field, no significant attraction is observed on this scale, but only the contact interactions.

Free beads may be micromanipulated with the cobalt bead of the AFM sensor. This cannot be done at the present time under the AFM itself owing to lack of optical access for monitoring the operation, but it may be simulated by means of a sensor attached to a micromanipulator in the field of an inverted optical microscope. An AFM integrated with an inverted microscope is under study. It is observed essentially that the free beads are attracted by the sensor within a radius of 1 or $2\mu$, and become stuck thereto. This is the most elementary means of sensing, which we plan to apply to the bead-DNA system. The force of linkage between the two beads is the sum of the force of magnetic attraction described above and a contact force, which is dependent essentially on the states of the surfaces: the linkage is fairly strong on an untreated sensor and cannot be readily broken. However, if the sensor is steeped in a solution of bovine serum albumin (BSA) (approximately 2%), the contact force is greatly decreased and the bead can be released by a sudden acceleration of the sensor or a brief rubbing against the substrate.

The operational device for analysis of DNA for the purpose of sequencing it is typically built around the transparent substrate (Nunc Covalink) onto which the DNA molecules are grafted. This substrate, is rigidly fixed to a piezoelectric or equivalent system, which moves it in the three directions in space. Above, a magnetic force sensor (AFM) permits quantitative measurements. Below, an optical microscope enables the surface and the force sensor to be observed in their relative movement. Lastly, the assembly is in the field of an electromagnet which, depending on the field applied, can layer the beads at the surface, thereby permitting magnetic imaging, move them away from the surface (removal of ungrafted beads in order to facilitate the operator's choice) or, with a zero field, allow the DNA to move about freely so that it becomes stuck to the sensor. In this configuration, quantitative measurement of the forces and sequencing of the DNA can be carried out.

EXAMPLE 4

This example deals with quantitative measurements of the force on the molecule during traction.

Three conditions must be satisfied: attaching magnetic beads to a glass plate by DNA molecules, being able to determine the number of molecules which join a bead to the glass plate so as to choose the ones which are joined by a bead, and finally, measuring the traction force on the molecule using an atomic force microscope (AFM).

Coupling of the DNA molecule follows a protocol similar to the one described above. The attachment of each of the ends of the DNA molecule takes place during separate steps; the purpose of this is to prevent both ends of a single molecule linking either to the bead or to the glass surface, forming a loop. The end to which it is desired to attach the magnetic bead is first grafted selectively with biotin, which will bind to streptavidin with which the magnetic bead is coated. The second end is attached to a digoxygenin molecule (DIG-dUTP), which forms a link with its anti-DIG antibody with which a glass plate previously treated with protein A has been coated.

Stretching of a DNA molecule

By bringing close a magnetized tip consisting of a cobalt bead, using a micromanipulator, it could be verified that a number of beads are captive and cannot move away further than a distance of 15 $\mu$m from their point of anchoring, which corresponds precisely to the length of the DNA molecule used.

Characterization of the sample

Figure 6A:
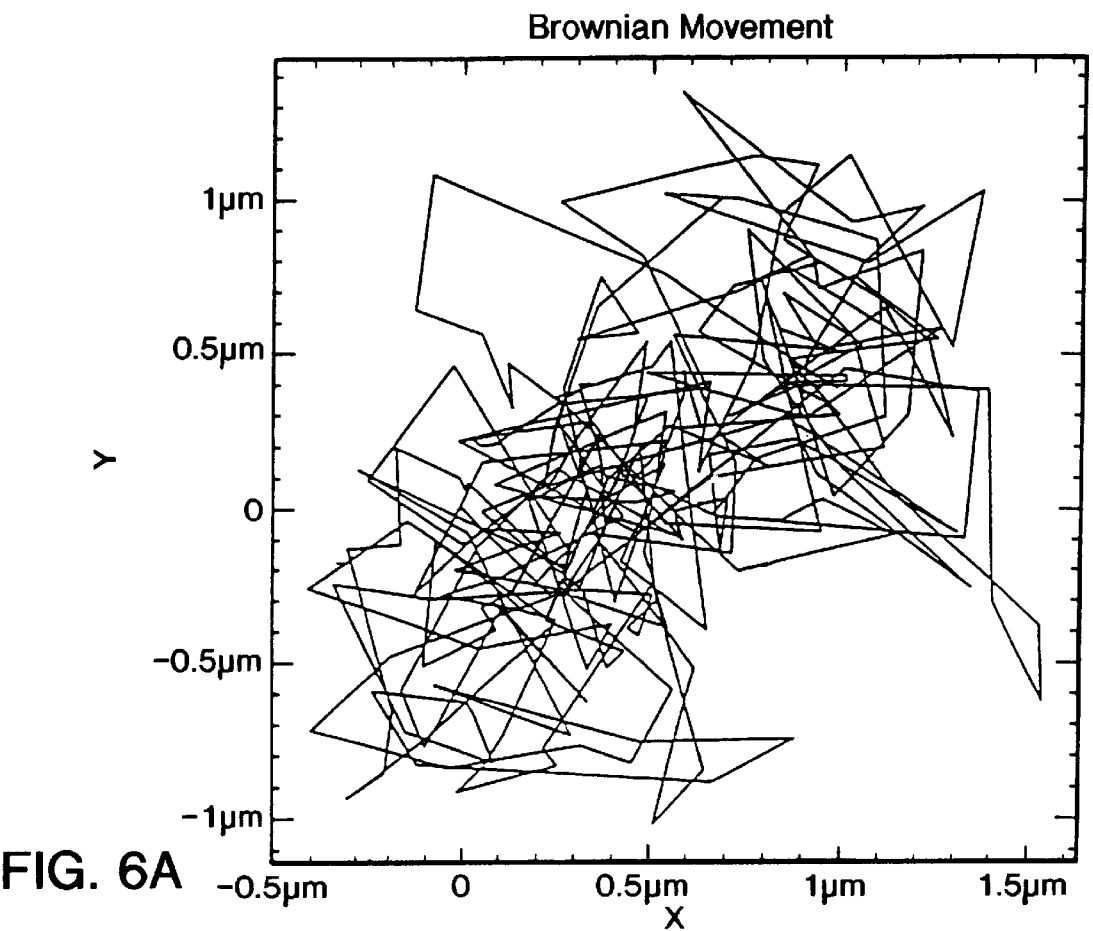
FIG. 6 shows the movements of the center of the bead over a little more than 5 minutes; at the top, movements in the plane of observation, at the bottom, time course of the position of the bead according to X with time.
Figure 6B:
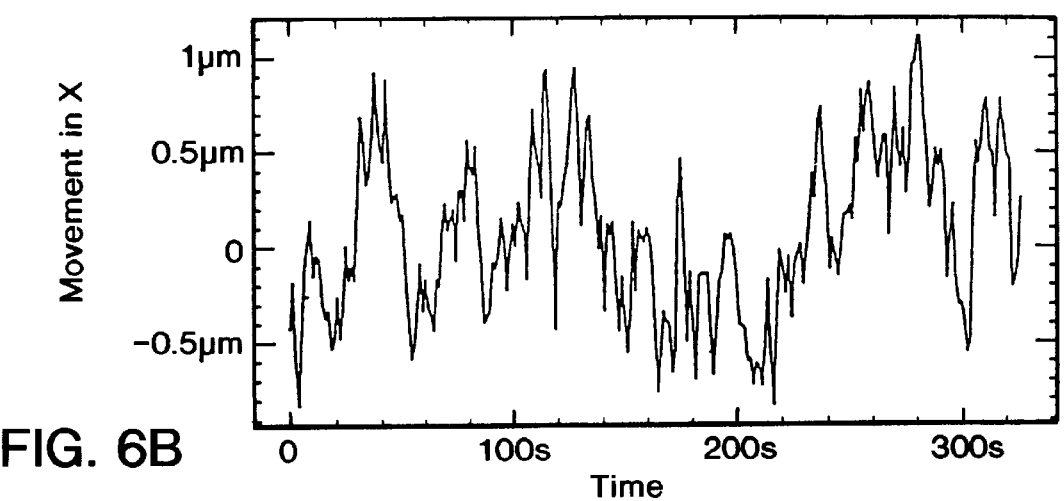

During the preparation of the sample, the number of DNA molecules that join a bead to the glass plate can vary; hence the number of molecules involved in the linkage must be determined a posteriori. A device was developed enabling this determination to be carried out without causing interference: the amplitude of the Brownian movements of the bead is measured, and the number of molecules, which join the latter to the glass plate, is deduced therefrom. In effect, the larger this number of molecules, the more firmly the bead is attached to the surface and the smaller the amplitude of these fluctuations. The appearance of the fluctuations observed, corresponding to the case where the bead is joined by a single DNA molecule, is reproduced in FIG. 6.

To determine the number of molecules, $<x^2>$ is measured and the following expression is used:

$$nk<x^2>=k_BT$$

where k is the stiffness of a DNA molecule, $k_B$ is the Boltzmann constant, T is the temperature and n is the number of molecules.

Breaking of a DNA molecule

Figure 7:
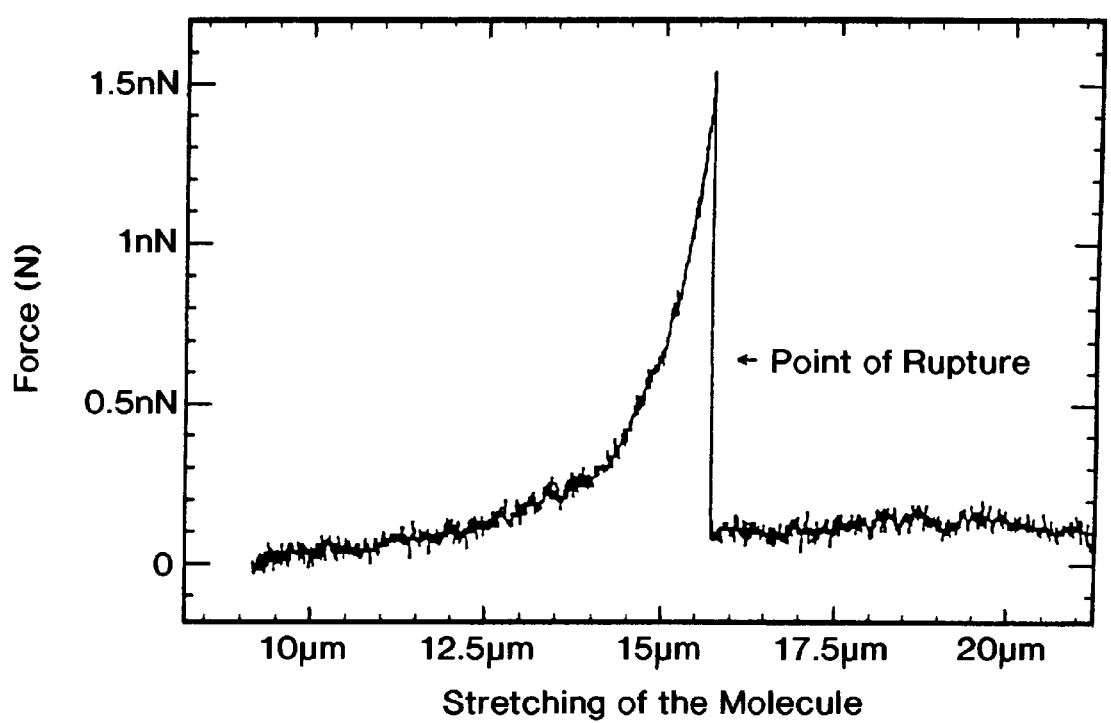
FIG. 7 shows a diagram of stretching of a $\lambda$ DNA molecule by extension using an atomic force microscope. When the molecule is almost completely extended, it exerts a force of the order of a few nN before breaking.

By increasing the magnetization of the colbalt bead stuck to the tip of the micromanipulator, the DNA molecule can then be broken by moving away the bead further than 15 $\mu$m. By repeating this experiment with the atomic force microscope, the tension force on the molecule at the time of rupture of the latter was measured (FIG. 7).

We claim:

1. A method of determining a sequence of a nucleic acid selected from double-stranded DNA and double-stranded RNA/DNA hybrid, comprising:
   (a) determining the energy of pairing or of unpairing between each base pair of the nucleic acid; and
   (b) comparing said energy with predetermined values.

2. The method according to claim 1, comprising:
   a) attaching at least one base of each strand of said nucleic acid to a support;
   b) moving away the supports so as to unpair, one after another, each base pair while measuring at each unpairing the energy needed for unpairing; and
   c) comparing it with predetermined values.

3. The method according to claim 1, comprising:
   a) attaching at least one base of each strand of said nucleic acid to a support;
   b) bringing the supports together so as to pair each base pair while measuring at each pairing the energy needed for pairing; and
   c) comparing said energy with predetermined values.

4. The method of claim 1, comprising:
   (a) determining a global energy needed to unpair the nucleic acid; and
   (b) comparing said global energy to the energy needed to unpair a reference sequence.

5. The method according to claim 1, wherein the identity of a base in a base pair in the nucleic acid is determined by comparison of said energy to predetermined values.

6. The method according to claims 2 or 3, wherein the ends of each strand of said nucleic acid, not attached to the supports, are joined to one another covalently or quasi-covalently.

7. The method according to claim 1, wherein the strands of the nucleic acid are repaired and then unpaired.

8. Method according to claims 2 or 3, wherein each strand of the nucleic acid is attached to the support by several bases.

9. The method according to claim 1, wherein one strand of the nucleic acid is attached directly or indirectly to a movable surface, and wherein the other strand of the nucleic acid is attached to force sensor.

10. The method according to claim 9, wherein the strand of the nucleic acid is attached to the movable surface by a magnetic force.

11. The method according to claim 9, wherein the force sensor is a lever of an atomic force microscope and the movable surface is a nanometric movement device.

12. The method according to claim 9, wherein the force sensor is a magnet controlled by a magnetic field.

13. The method according to claim 9, wherein the force sensor is a lever or a membrane in combination with a movement sensor.

14. The method according to claim 1, wherein one strand of the nucleic acid is placed in a vessel containing the other strand of the nucleic acid attached to a support and the strands are contacted to form a hybrid, and the base pair energy of a base pair in the hybrid is determined.

15. The method according to claim 1, wherein one strand of the nucleic acid is DNA.

16. The method according to claim 1, wherein the nucleic acid sequence in a test sample is determined by the base pair energy.

17. A method of sequencing a nucleic acid sequence, wherein the method comprises:
   (a) determining the energy of pairing or of unpairing between each base pair of a first nucleic acid sequence to a second nucleic acid sequence; and
   (b) identifying the sequence of the nucleic acid sequence through the comparison of said energy of pairing or unpairing with predetermined base pair energy values.

18. The method of claim 17, wherein at least one base of each nucleic acid sequence is attached to a support.

19. The method of claim 18, wherein the supports are moved away in order to unpair the nucleic acid sequences.

20. The method of claim 18, wherein the supports are brought together to pair the nucleic acid sequences.

21. The method of claim 18, wherein the ends of the nucleic acid sequences, which are not attached to the supports, are joined to one another covalently or quasi-covalently.

22. The method of claim 17, wherein the first and second nucleic acid sequences are re-paired and then unpaired.

23. The method of claim 19, wherein either or both of the nucleic acid sequences are attached to the support by several bases.

24. The method of claim 17, wherein one of the nucleic acid sequences is attached directly or indirectly to a movable surface, and wherein the other nucleic acid sequence is attached to a force sensor.

25. The method of claim 24, wherein the attachment of the nucleic acid sequence to the movable surface is by a magnetic force.

26. The method of claim 24, wherein the force sensor is a lever of an atomic force microscope and the movable surface is a nanometric movement device.

27. The method of claim 24, wherein the force sensor is a magnet controlled by a magnetic field.

28. The method of claim 24, wherein the force sensor is a lever or a membrane in combination with a movement sensor.

29. The method of claim 17, wherein the first or the second nucleic sequence is placed in a vessel containing the other nucleic acid sequence.

30. The method of claim 17, wherein nucleotide sequence of the first or the second nucleic acid sequence is unknown.

31. The method of claim 17, wherein the nucleic acid sequence is determined from the global energy.

32. The method of claim 17, wherein either or both of the nucleic acid sequences are DNA.

33. The method of claim 17, wherein either or both of the nucleic acid sequences are RNA.

34. A method of determining base pair energy of nucleotides in a nucleic acid sequence, wherein the method comprises determining the energy of pairing or of unpairing between each base pair of a first nucleic acid sequence to a second nucleic acid sequence.

35. The method according to claim 34, wherein at least one base of each nucleic acid sequence is attached to a support.

36. The method according to claim 35, wherein the supports are either moved away or brought together in order to unpair or pair each nucleotide base pair of the nucleic acid sequences.

37. The method according to claim 35, wherein the ends of the nucleic acid sequences, not attached to the supports, are joined to one another covalently or quasi-covalently.

38. The method according to claim 34, wherein the first and second nucleic acid sequences are re-paired and then unpaired.

39. The method according to claim 35, wherein either nucleic acid sequence is attached to the support by several bases.

40. The method according to claim 34, wherein either one of the nucleic acid sequences is attached directly or indirectly to a movable surface, and wherein the other nucleic acid sequence is attached to a force sensor.

41. The method according to claim 40, wherein the nucleic acid sequence is attached to the movable surface by a magnetic force.

42. The method according to claim 40, wherein the force sensor is a lever of an atomic force microscope and the movable surface is a nanometric movement device.

43. The method according to claim 40, wherein the force sensor is a magnet controlled by a magnetic field.

44. The method according to claim 40, wherein the force sensor is a lever or a membrane in combination with a movement sensor.

45. The method according to claim 34, wherein either one of the nucleic sequences is placed in a vessel containing the other nucleic acid sequence attached to a support and the nucleic acid sequences are contacted to form a hybrid, and the base pair energy of a nucleotide in the hybrid is determined.

46. The method according to claim 34, wherein either one of the nucleic acid sequences is DNA.

47. The method of claim 34, wherein the nucleotide sequence of the first or the second nucleic acid sequence is unknown.

48. The method of claim 34, wherein either or both of the nucleic acid sequences are RNA.

49. A method of detecting the presence of a first nucleic acid in a sample, wherein the method comprises:

(a) contacting the sample with a second nucleic acid;

(b) determining the energy of pairing or of unpairing between the first nucleic acid and the second nucleic acid; and (c) detecting the first nucleic acid by comparing said energy of pairing or unpairing with predetermined energy values as an indicator of the presence of the first nucleic acid in the sample.

50. The method of claim 49, wherein at least one base of each nucleic acid is attached to a support.

51. The method of claim 50, wherein the supports are moved away in order to unpair the nucleic acids.

52. The method of claim 50, wherein the supports are brought together to pair the nucleic acids.

53. The method of claim 50, wherein the ends of the nucleic acids, which are not attached to the supports, are joined to one another covalently or quasi-covalently.

54. The method of claim 49, wherein the first and second nucleic acids are re-paired and then unpaired.

55. The method of claim 50, wherein either or both of the nucleic acids are attached to the support by several bases.

56. The method of claim 49, wherein one of the nucleic acids is attached directly or indirectly to a movable surface, and wherein the other nucleic acid is attached to a force sensor.

57. The method of claim 56, wherein the attachment of the nucleic acid to the movable surface is by a magnetic force.

58. The method of claim 56, wherein the force sensor is a lever of an atomic force microscope and the movable surface is a nanometric movement device.

59. The method of claim 56, wherein the force sensor is a magnet controlled by a magnetic field.

60. The method of claim 56, wherein the force sensor is a lever or a membrane in combination with a movement sensor.

61. The method of claim 49, wherein the first or the second nucleic acids is placed in a vessel containing the other nucleic acid.

62. The method of claim 49, wherein nucleotide sequence of the first or the second nucleic acid is unknown.

63. The method of claim 49, wherein either or both of the nucleic acids are DNA.

64. The method of claim 49, wherein either or both of the nucleic acids are RNA.

65. A method of determining the global energy of a nucleic acid sequence, comprising:

(a) determining the global energy needed to unpair the nucleic acid sequence from a second nucleic acid sequence; and (b) comparing said global energy to the energy needed to unpair a reference sequence.

66. The method of claim 65, wherein at least one base of each nucleic acid sequence is attached to a support.

67. The method of claim 66, wherein the supports are moved away in order to unpair the nucleic acid sequences.

68. The method of claim 66, wherein the supports are brought together to pair the nucleic acid sequences.

69. The method of claim 66, wherein the ends of the nucleic acid sequences, which are not attached to the supports, are joined to one another covalently or quasi-covalently.

70. The method of claim 65, wherein the first and second nucleic acid sequences are re-paired and then unpaired.

71. The method of claim 67, wherein either or both of the nucleic acid sequences are attached to the support by several bases.

72. The method of claim 65, wherein one of the nucleic acid sequences is attached directly or indirectly to a movable surface, and wherein the other nucleic acid sequence is attached to a force sensor.

73. The method of claim 72, wherein the attachment of the nucleic acid sequence to the movable surface is by a magnetic force.

74. The method of 72, wherein the force sensor is a lever of an atomic force microscope and the movable surface is a nanometric movement device.

75. The method of claim 72, wherein the force sensor is a magnet controlled by a magnetic field.

76. The method of claim 72, wherein the force sensor is a lever or a membrane in combination with a movement sensor.

77. The method of claim 65, wherein the first or the second nucleic sequence is placed in a vessel containing the other nucleic acid sequence.

78. The method of claim 65, wherein nucleotide sequence of the first or the second nucleic acid sequence is unknown.

79. The method of claim 65, wherein either or both of the nucleic acid sequences are DNA.

80. The method of claim 65, wherein either or both of the nucleic acid sequences are RNA.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGGCGGCGAC CT          12

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGGCGGCGAC CTGGGGGGGG G          21

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGGTCGCCGC CCT          13

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGGTCGCCGC CC          12

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TTTTTTTTGG GCGGCGACCT                                                                                   20

(2) INFORMATION FOR SEQ ID NO:6:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:6:

GGGCGGCGAC CTGGGGGGGG G                                                                                 21

(2) INFORMATION FOR SEQ ID NO:7:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:7:

AGGTGCCGCC CAAAAAAAA                                                                                    19

(2) INFORMATION FOR SEQ ID NO:8:

(i) SEQUENCE CHARACTERISTICS:
  (A) LENGTH: 12 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:8:

AGGTCGCCGC CC                                                                                           12

(2) INFORMATION FOR SEQ ID NO:9:

(i) SEQUENCE CHARACTERISTICS:
  (A) LENGTH: 12 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:9:

AGGTCGCCGC CC                                                                                           12

(2) INFORMATION FOR SEQ ID NO:10:

(i) SEQUENCE CHARACTERISTICS:
  (A) LENGTH: 12 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:10:

GGGCGGCGAC CT                                                                                           12